(12) United States Patent
Yaegashi et al.

(10) Patent No.: US 6,743,918 B2
(45) Date of Patent: Jun. 1, 2004

(54) PROCESS FOR PRODUCING CAMPTOTHECIN

(75) Inventors: Takashi Yaegashi, Tokyo (JP); Takanori Ogawa, Tokyo (JP); Seigo Sawada, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 31 days.

(21) Appl. No.: 10/239,113

(22) PCT Filed: Mar. 21, 2001

(86) PCT No.: PCT/JP01/02216
§ 371 (c)(1),
(2), (4) Date: Nov. 25, 2002

(87) PCT Pub. No.: WO01/70747
PCT Pub. Date: Sep. 27, 2001

(65) Prior Publication Data
US 2004/0087609 A1 May 6, 2004

(30) Foreign Application Priority Data
Mar. 22, 2000 (JP) .......................................... 2000-79385

(51) Int. Cl.⁷ .................... C07D 491/12; C07D 491/22; A61K 31/936
(52) U.S. Cl. ......................................... 546/48; 514/280
(58) Field of Search ............................. 546/48; 514/280

(56) References Cited

U.S. PATENT DOCUMENTS

| 4,496,555 A | 1/1985 | Brooks et al. |
| 4,568,673 A | 2/1986 | Brooks et al. |
| 4,604,463 A | * 8/1986 | Miyasaka et al. ............ 544/125 |
| 4,868,291 A | 9/1989 | Saulnier et al. |

FOREIGN PATENT DOCUMENTS

| EP | 0230270 A2 | 7/1987 |
| JP | 61085319 A | 4/1986 |
| JP | 01131179 A | 5/1989 |
| JP | 01186892 A | 7/1989 |
| JP | 08073461 A | 3/1996 |
| JP | 11140085 A | 5/1999 |

* cited by examiner

*Primary Examiner*—Rita Desai
(74) *Attorney, Agent, or Firm*—Wolf, Greenfield & Sacks, P.C.

(57) ABSTRACT

Problem: A large scale production of camptothecin, which is a starting compound of irinotecan hydrochloride and various camptothecin derivatives, at a low cost and with ease.

Solution: A process for preparing camptothecin, characterized in that it comprises the following steps (a) and (b);

(a) the step to hydrolyze 9-methoxycamptothecin or a natural material containing 9-methoxycamptothecin;

(b) the step to convert 9-hydroxycamptothecin obtained in the step (a) into camptothecin by 9-O—perfluoro-lower-alkylsulfonylation or 9-O—phenyltetrazolylation, followed by hydrogenolysis.

4 Claims, No Drawings

PROCESS FOR PRODUCING CAMPTOTHECIN

RELATED APPLICATIONS

This application is a national stage filing under 35 U.S.C. § 371 of PCT application PCT/JP01/02216, filed Mar. 21, 2001.

DETAILED DESCRIPTION OF THE INVENTION

1. Technical Field of the Invention

The present invention relates to a novel process for preparing camptothecin useful as a starting material for irinotecan hydrochloride and various camptothecin derivatives as anti-tumor agents.

2. Description of the Prior Art

Camptothecin (hereinafter referred to CPT) is a pentacyclic alkaloid which is isolated from natural materials such as *Camtotheca acuminata* Nyssaceae of Chinese origin, and various kinds of useful semi-synthetic derivatives with anti-tumor activities prepared from this as a starting material have been provided by the exploratory researches of the present inventors (see for example, JP, A, 1-186892; JP, A, 1-131179; JP, A, 8-73461; JP, A, 11-140085 and others).

7-Ethyl-10-piperidinopiperidinocarbonyloxycamptothecin (hereinafter referred to as CPT-11) is a compound with high anti-tumor activity and low toxicity, and is now broadly sold as an anti-tumor agent (general name; irinotecan hydrochloride). Further, among CPT-11 analogues, there are many known to have similar anti-tumor effect.

However, owing to an extremely low amount of CPT obtained from natural materials such as *Camtotheca acuminata* Nyssaceae, it is anticipated that a sufficient supply of CPT will become difficult, despite the on going a measure for sufficient providing starting materials, such as afforestation, to catch up the increased demand for useful derivatives, such as CPT-11, and the like. Although the total syntheses have also been examined, because of many problems in terms of equipments, yields and costs and the like, the present situation is that it has yet to be into practical use.

Problems to be Solved by the Invention

Accordingly, it is the object of the invention to produce CPT, which is a starting compound of irinotecan hydrochloride and various camptothecin derivatives, at a low cost and with ease.

Means for Solving Problem

During the extensive researches made to solve the above problems, the inventors focused their attention on the so far discarded CPT analogues contained in natural materials such as *Camtotheca acuminata* Nyssaceae and then investigated that 9-methoxycamptothecin (hereinafter referred to as 9-MC) had been obtained, unexpectedly, as a by-product of the CPT production in a considerable amount. As a starting material and to supply CPT steadily as a result of continuing research to utilize this further, the inventors found out means to prepare CPT, easily and efficiently from 9-MC and thus accomplished the invention.

Accordingly, the invention relates to a process for preparing camptothecin, characterized in that it comprises the following steps (a) and (b);

(a) the step to hydrolyze 9-methoxycamptothecin or a natural material containing 9-methoxycamptothecin;

(b) the step to convert 9-hydroxycamptothecin obtained in the step (a) into camptothecin by 9-O-perfluoro-lower-alkylsulfonylation or 9-O-phenyltetrazolylation, followed by hydrogenolysis.

Further, the invention relates to the above process, characterized in that, in the step (b), 9-hydroxycamptothecin is subjected to 9-O-trifluoromethanesulfonylation.

Furthermore, the invention relates to the process for preparing the above camptothecin, wherein 9-hydroxycamptothecin is the 20(S) isomer and camptothecin is 20(S)-camptothecin.

In the invention, 9-MC as the starting compound of CPT, can be used are those isolated and purified from various natural materials, those chemically converted from analogous compounds, or natural materials containing 9-MC themselves. Illustrative of the natural materials containing 9-MC are, for example, *Camtotheca acuminata* Nyssaceae, *Nothapodytes foetida, Ervatamia heyneana, Ophiorrhiza japonica*, though it is preferred that *Nothapodytes foetida* is used, due to its high content of 9-MC, particularly in *Nothapodytes foetida*. In case these natural materials are used, first they are untreated, or subjected to a treatment such as cutting and crushing, followed by extraction with an organic solvent such as methanol, ethanol, acetone, ethyl acetate, chloroform-methanol mixture and dichloromethane-methanol mixture. Thus—obtained extract is dried and may be used as it is, or the one appropriately purified by means of column chromatography, recrystallization or reprecipitation may be used.

In the invention, 9-MC or a natural material containing 9-MC is first converted to 9-hydroxycamptothecin hereinafter referred to "9-HC" by hydrolysis. Methods for conversion include a method to treat with iodotrimethylsilane in quinoline, chloroform or the like, a method to heat with sodium ethylmercaptan, potassium thiophenoxide, sodium thiocresolate or the like using dimethylformamide as a solvent, a method to heat with sodium cyanide in dimethyl sulfoxide, a method to treat with boron trichloride, boron tribromide or boron tribromide-dimethylsulfide complex in dichloromethane or 1,2-dichloroethane, a method to heat with pyridine hydrochloride, a method to treat with aluminum chloride, a method to treat with trifluoromethanesulfonic acid in the presence of thioanisole, a method to heat with 57% hydroiodic acid (here the reaction can be carried out in the presence of red phosphorus), a method to heat with 47% hydrobromic acid (here an auxiliary solvent such as acetic acid or dioxane may be used) and the like, and in particular it is preferable to use a method to reflux with 47% hydrobromicacid, which is efficient, inexpensive and simple.

Subsequently, 9-HC obtained in the above reaction is converted to CPT. Illustrative of methods for conversion are a method to lead 9-HC to the triflate ($OSO_2CF_3$: OTf) and to hydrogenolyze, a method to lead to the nonaflate ($OSO_2C_4F_9$: ONf) and to hydrogenolyze, and a method to lead to the 1-phenyl-5-tetrazolyloxy derivative (OTz) and to hydrogenolyze and the like.

CPT can be obtained by any of the above CPT conversion methods, though in particular, from the point that CPT can be prepared by short steps in which the procedures are simple, reagents used are inexpensive, in actually the hydrogenolysis step inexpensive formic acid can be used of hydrogen gas as hydrogen source, and further heating and stirring can be made in a usual reaction apparatus, and from the point that each step proceeds in a good yield, it is preferred that 9-HC is treated with trifluoromethanesulfonyl chloride, trifluoromethanesulfonic acid anhydride, N-phenyl trifluoromethanesulfonimide or the like, leading to 9-trifluoromethanesulfonyloxycamptothecin (hereinafter referred to 9-OTfC) and further 9-OTfC is converted to CPT by hydrogenolysis, using palladium catalyst and formic acid as a hydrogen source, in the presence of a tertiary amine such as triethylamine or n-tributylamine.

Mode for Carrying Out the Invention

In the following, the mode for carrying out the process for preparing CPT using 9-MC as a starting material in the invention is illustrated. However, the invention is not limited by this.

The figure below is the scheme for the conversion of 9-MC to CPT.

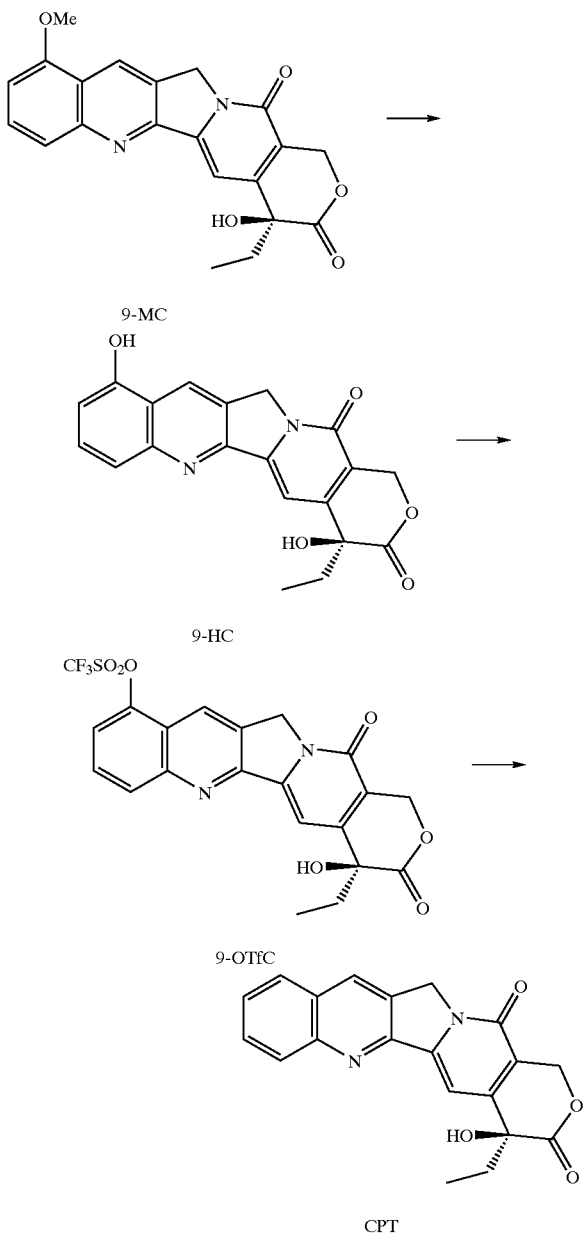

The preferable embodiment for converting 9-MC to CPT comprises the following three steps:
1. the preparation step for 9-hydroxycamptothecin (9-HC);
2. the preparation step for 9-trifluoromethanesulfonyl-oxycamptothecin (9-OTfC);
3. the preparation step for camptothecin (hydrogenolysis of 9-OTfC).

To illustrate in more detail, specifically, in step 1 9-methoxycamptothecin (9-MC) is suspended in 47% hydrobromic acid, degassed under reduced pressure and heated under stirring after displacement by argon gas to give 9-HC. The amount used for 47% hydrobromic acid is in the range of 10 ml to 100 ml based on 1 g, preferably in the range of 15 ml to 25 ml. Temperature for heating is in the range of 100° C. to 180° C., preferably in the range of 160° C. to 180° C. Further, as to the reaction period, it is in the range of 1 hr to 24 hr, and heating for 3–4 hr is preferred.

9-MC, starting material, may be used without particular purification.

Further in this step, other known methods generally used in hydrolysis of aromatic methoxyl group can also be used.

In step 2, the above 9-HC was added with 1.0–5.0 equivalents of N-phenyl trifluoromethanesulfonimide, trifluoromethanesulfonyl chloride or trifluoromethanesulfonic acid anhydride in the presence of a base using N,N-dimethylformamide, dichloromethane or chloroform as a solvent, and was reacted at ice-cooling to 100° C. for 0.5–3 hr to give 9-OTfC. This reaction is preferably carried out in an inactive gas atmosphere such as argon gas. The starting material, 9-HC, may be used after isolation as it is, or an appropriately purified material by means such as column chromatography, recrystallization or reprecipitation may be used.

Illustrative of the base are organic bases such as triethylamine, n-butylamine, pyridine and N,N-dimethylaminopyridine, or alkaline metal salts such as sodium carbonate, potassium carbonate, sodium hydrogen carbonate and potassium hydrogen carbonate. Preferably, 1.5–3.5 equivalent amounts of N-phenyl trifluoromethane-sulfonimide is used in the presence of 3.0–7.0 equivalents of triethylamine using N,N-dimethylformamide as solvent and heated at 50° C. to 60° C. for 0.5–1 hr to give 9-OTfC almost quantitatively. Further, as a trifluoromethanesulfonylating agent, the solvent such as dichloromethane or chloroform is preferable in case of use of trifluoromethanesulfonyl chloride or trifluoromethanesulfonic acid anhydride.

In step 3, 9-OTfC is added with formic acid as a hydrogen source in N,N-dimethylformamide as a solvent using palladium catalyst in the presence of base, stirred under argon gas atmosphere at 40° C.–80° C. for 1–18 hr, and hydrogenolyzed to give CPT. In this case, addition of molecular sieve 3 Å (MS3 Å) can accelerate the reaction.

The base includes, for example, a tertiary amine such as triethylamine or n-tributylamine, and can be used in the range of 3–20 equivalents. Formic acid can be used in the range of 2–10 equivalents. Illustrative of the palladium catalyst are, for example, palladium acetate ($Pd(OAc)_2$)-triphenylphosphine ($Ph_3P$), palladium acetate-1,1'-bis(diphenylphsphino)ferrocene (DPPF), palladium acetate-tri-n-butylphosphine (n-$Bu_3P$), tetrakis(triphenylphosphine) palladium ($Pd(PPh_3)_4$) and dichlorobis (triphenylphosphine) palladium ($PdCl_2(PPh_3)_2$). The palladium catalyst can be used in the range of 4–50 mole %. In case of palladium acetate, phosphine ligand is added in the range of 8–100 mole %. Further, in the presence of the palladium catalyst the reaction can be carried our using N,N-dimethylformamide as a solvent, potassium carbonate as a base and borane-dimethylamine complex as a hydrogen source.

Preferably, as a palladium catalyst, palladium acetate in 3–6 mole % and triphenylphosphine in 6–12 mole %, or dichlorobis (triphenylphosphine) palladium in 5–15 mole % is used, added with triethylamin as the base in 3–14 equivalents and formic acid in 1.5–7 equivalents, and desirably reacted under an inactive gas atmosphere such as argon gas at near 60° C. for 2–6 hr.

In this hydrogenolysis step, after triflate forming reaction, 9-OTfC can be used without isolation, or an appropriately purified material by means such as column chromatographic method or recrystallization can be used.

Further, as for the starting compound, the intermediate compound and the target compound, their stereoisomers, optical isomers, tautomeric isomers and the like are involved.

EXAMPLES

In the following, the invention will be illustrated in more detail by way of examples, but the invention is not limited in any way by them.

Example 1

Preparation of 9-hydroxycamptothecin (9-HC)

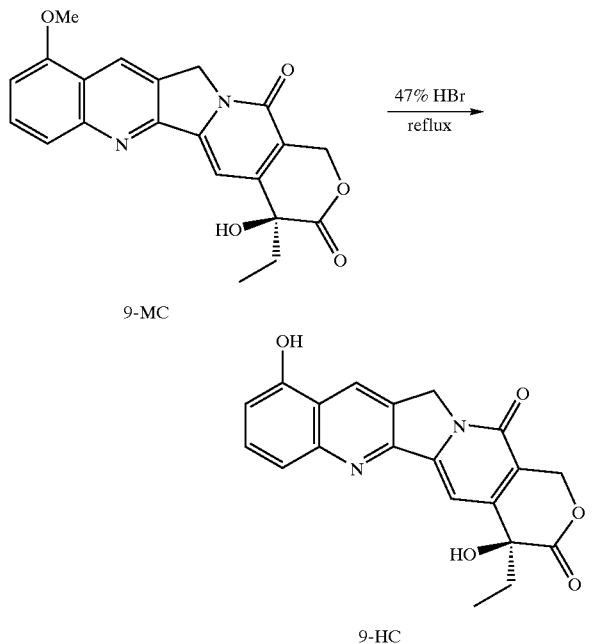

9-Methoxycamptothecin (9-MC; 10.0 g, 26.43 mmol) was suspended in 47% hydrobromic acid (200 ml), degassed by suction and then displaced by argon gas, and refluxed for 3.5 hr. The reaction mixture was cooled to ambient temperature and poured into water (900 ml) in portion wise under stirring. The deposit was collected on a celite pad and washed with water. The obtained material by filtration was dissolved in chloroform containing 20% methanol, added with active carbon (20 g) and anhydrous sodium sulfate, stirred for 1 hr, filtered, concentrated to dryness under reduced pressure to give a crude product. The crude product was purified through silica gel column chromatography (chloroform containing 8% methanol) to give 9-hydroxycamptothecin (9-HC) as a brown solid; mp 231–237° C. (decomposition) (6.47 g, yield 67%).

In the following, the NMR spectrum, IR spectrum and MS spectrum are shown.

$^1$H-NMR (DMSO-d$_6$) δ: 0.87 (3H, t, J=7 Hz, 20-CH$_2$CH$_3$), 1.78–1.98 (2H, m, 20-CH$_2$CH$_3$), 5.26 (2H, s), 5.42 (2H, s), 6.73–7.46 (1H, br, D$_2$O exchangeable), 7.03 (1H, d, J=7 Hz), 7.32 (1H, s, 14-H), 7.52–7.70 (2H, m), 7.83 (1H, s, 7-H), 10.50–10.92 (1H, br, D$_2$O exchangeable).

IR (KBr): 3390, 3121, 1749, 1657, 1616, 1591 cm$^{-1}$.

EI-MS m/z: 364 (M$^+$).

Example 2

Preparation of 9-trifluoromethanesulfonyloxycamptothecin (9-OTfC)

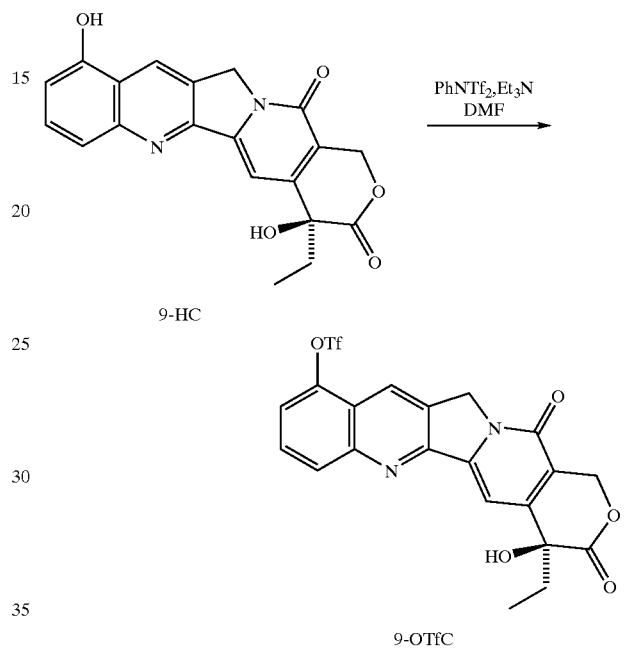

To a solution of 9-hydroxycamptothecin (9-HC; 300 mg, 0.82 mmol) in N,N-dimethylformamide (8 ml) was added with triethylamine (0.34 ml, 2.47 mmol, 3.0 eq) and N-phenyl trifluoromethanesulfonimide (442 mg, 1.24 mmol. 1.5 eq) and stirred at ambient temperature under argon gas atmosphere for 0.5 hr. After confirming the disappearance of the starting material by thin layer chromatography (chloroform:methanol=20:1), the solvent was evaporated under reduced pressure. The residue was added with chloroform (200 ml) and water (100 ml), and the separated organic phase was dried over anhydrous sodium sulfate, followed by evaporation of the solvent under reduced pressure. The residue was dissolved in chloroform (5 ml) and added with n-hexane (50 ml). The deposit was subjected to a suction filtration and dried under reduced pressure to give 9-trifluoromethanesulfonyloxycamptothecin (9-OTfC) as a pale yellow solid; mp 263–266° C. (decomposition) (350 mg, yield 86%).

In the following, the NMR spectrum, IR spectrum and MS spectrum are shown.

$^1$H-NMR (400 MHz, CDCl$_3$) δ: 1.05 (3H, t, J=7 Hz), 1.83–1.96 (2H, m), 3.77 (1H, s), 5.32 (1H, d, J=17 Hz), 5.38 (2H, s), 5.76 (1H, d, J=17 Hz), 7.65 (1H, d, J=8 Hz), 7.71 (1H, s), 7.87 (1H, t, J=8 Hz), 8.30 (1H, d, J=8 Hz), 8.62 (1H, s).

IR (KBr): 3387, 1751, 1663, 1626, 1607 cm$^{-1}$.

EI-MS m/z: 496 (M$^+$).

Example 3

Preparation of Camptothecin (CPT) (Hydrogenolysis of 9-OTfC)

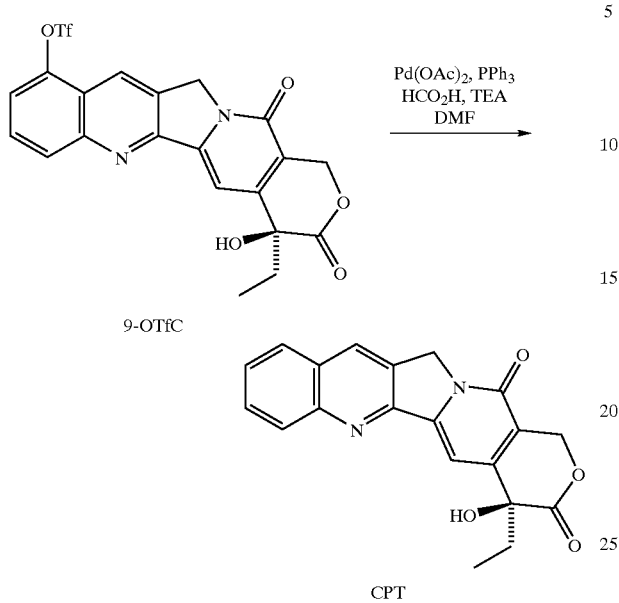

To a stirred solution of 9-trifluoromethanesulfonyloxycamptothecin (9-OTfC; 100 mg, 0.20 mmol) in N,N-dimethylformamide (5 ml), triethylamine (61 mg, 0.606 mmol. 3.0 eq.), palladium acetate (2 mg, 0.0081 mmol. 4 mol %), triphenylphosphine (4 mg, 0.0162 mmol. 8 mol %) and formic acid (19 mg, 0.404 mmol, 2.0 eq.) were added at ambient temperature and the mixture was stirred at 60° C. for 1 hr under argon gas atmosphere. The disappearance of the starting material was confirmed by thin layer chromatography (chloroform:methanol=50:1) and the solvent was evaporated under reduced pressure. The residue was added with chloroform (5 ml) and n-hexane (200 ml), and the resulting precipitate was taken by suction filteration to give camptothecin (CPT) (44 mg, yield 63%) as a yellow solid.

In the following, the NMR spectrum is shown.

$^1$H-NMR (400 MHz, DMSO-$d_6$) δ: 0.88 (3H, t, J=7 Hz), 1.83–1.90 (2H, m), 5.29 (2H, s), 5.42 (2H, s), 6.53 (1H, s), 7.35 (1H, s), 7.69–7.73 (1H, m), 7.84–7.88 (1H, m), 8.12–8.18 (2H, m), 8.69 (1H, s).

Example 4

Preparation of Camptothecin from 9-HC by One-pot reaction

To a solution of 9-hydroxycamptothecin (9-HC; 300 mg, 0.82 mmol) in N,N-dimethylformamide (15 ml), triethylamine (0.68 ml, 4.92 mmol. 6.0 eq.) and N-phenyl trifluoromethanesulfonimide (879 mg, 2.46 mmol, 3.0 eq.) were added, and the mixture was stirred at 60° C. for 0.5 hr under argon gas atmosphere. After confirmation of the disappearance of the starting material by thin layer chromatography (chloroform:methanol=20:1), this reaction solution was added with triethylamine (1.14 ml, 8.20 mmol. 10.0 eq.), dichlorobis(triphenylphosphine)palladium (58 mg, 0.08 mmol, 10 mol %), formic acid (189 mg, 4.10 mmol, 5.0 eq.) and heated at 60° C. for 3 hr. After the disappearance of 9-OTfC was confirmed by thin layer chromatography (chloroform:methanol=50:1), and the reaction mixture was cooled, followed by evaporation of the solvent under reduced pressure. The residue was added with chloroform (5 ml) and n-hexane (200 ml) and the resulting precipitate was taken by suction filtration to give camptothecin (CPT) (209 mg, yield 73%) as a yellow solid.

Example 5

Preparation of 9-nonafluorobutanesulfonyloxycamptothecin (9-ONfC)

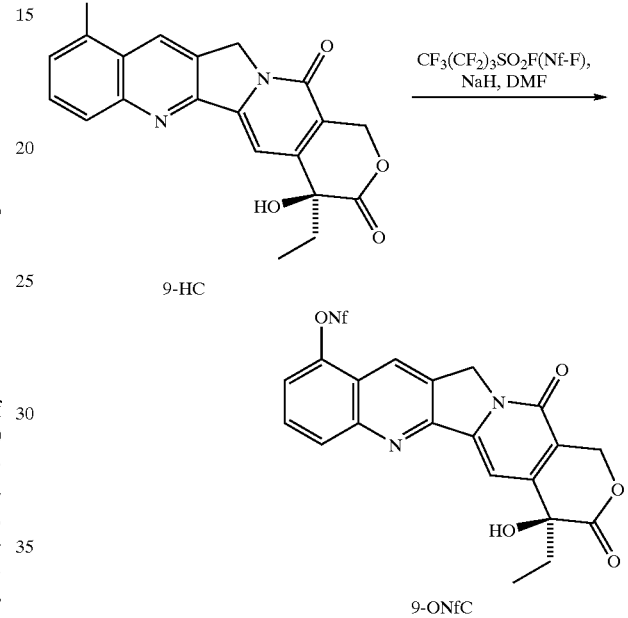

To a solution of 9-hydroxycamptothecin (9-HC; 180 mg, 0.49 mmol) in N,N-dimethylformamide (15 ml), sodium hydride (60% dispersion in mineral oil) (30 mg, 0.74 mmol, 1.5 eq.) and nonafluorobutanesulfonylfluoride (243 mg, 0.74 mmol, 1.5 eq.) were added at ambient temperature under argon gas atmosphere, and the mixture was stirred for 2 hr. The reaction solution was poured into a purified water (200 ml) under stirring, followed by addition of chloroform (200 ml) and 0.1 N HCl (50 ml). The precipitate was filtered off and the organic layer of the filtrate was taken, washed with purified water and a saturated aqueous sodium chloride (each 100 ml), dried over anhydrous sodium sulfate and followed by evaporation of the solvent under reduced pressure. The residue was purified through silica gel column chromatography (chloroform containing 1% methanol) to give 9-nonafluorobutanesulfonyloxycamptothecin (9-ONfC) as a yellow solid; mp 260–262° C. (decomposition) (85 mg, yield 27%).

In the following, the NMR spectrum, IR spectrum and MS spectrum are shown.

$^1$H-NMR (400 MHz, CDCl$_3$) δ: 1.05(3H, t, J=7 Hz), 1.85–1.96 (2H, m), 3.74 (1H, s), 5.32 (1H, d, J=17 Hz), 5.38 (2H, s), 5.77 (1H, d, J=17 Hz), 7.67 (1H, d, J=8 Hz), 7.70 (1H, s), 7.85–7.89 (1H, m), 8.30 (1H, d, J=9 Hz), 8.63 (1H, s). IR (KBr): 3396, 1755, 1663, 1603 cm$^{-1}$.

EI-MS m/z: 646 (M$^+$).

Example 6

Preparation of Camptothecin (CPT) (Hydrogenolysis of 9-ONfC)

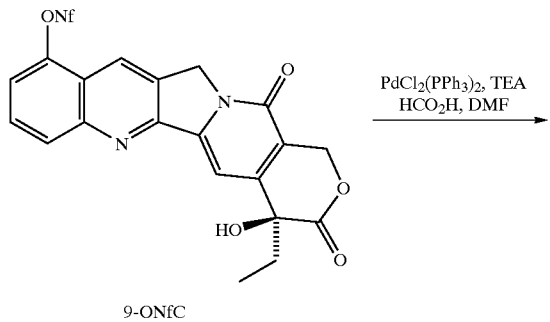

To a solution of 9-nonafluorobutanesulfonyloxycamptothecin (9-ONfC; 50 mg, 0.077 mmol) in N,N-dimethylformamide (3 ml), triethylamine (107 μl, 0.77 mmol, 10.0 eq.), dichlorobis(triphenylphosphine) palladium (5 mg, 0.0077 mmol, 10 mol %) and formic acid (15 μl, 0.39 mmol, 5.0 eq.) were added successively, and the mixture was stirred at 60° C. for 0.5 hr under argon gas atmosphere. The solvent was evaporated under reduced pressure. The residue was added with acetone (20 ml), and the resulting precipitate was taken by suction filtration to give camptothecin (CPT) (25 mg, yield 93%).

Example 7

Preparation of 9-(1-phenyl-5-tetrazolyloxy)camptothecin (9-OTzC)

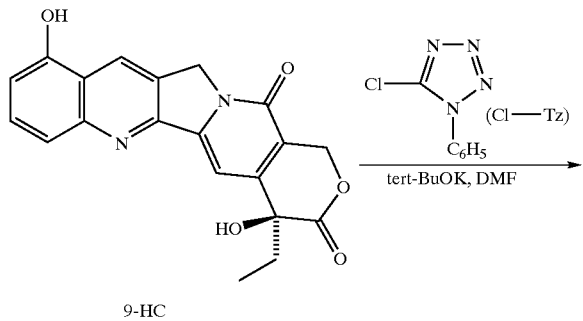

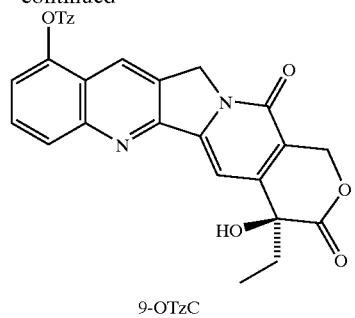

9-OTzC

To a solution of 9-hydroxycamptothecin (9-HC; 560 mg, 1.54 mmol) in dry N,N-dimethylformamide (50 ml) potassium tert-butoxide (208 mg, 1.85 mmol, 1.2 eq.) was added at ambient temperature under argon gas atmosphere. After stirring for 10 min, the solution was added with 5-chloro-1-phenyltetrazole (334 mg, 1.85 mmol, 1.2 eq.) and stirred for 6 hr. After evaporation of solvent under reduced pressure, the residue was extracted with chloroform, and the insoluble material was filtered off. The extract was evaporated to dryness under reduced pressure, and the residue was purified through silica gel column chromatography (ethyl acetate containing 1% methanol) to give 9-(1-phenyl-5-tetrazolyloxy)camptothecin (9-OTzC) as a yellow solid; mp 169–175° C. (decomposition) (375 mg, yield 48%).

In the following, the NMR spectrum, IR spectrum and MS spectrum are shown.

$^1$H-NMR (400MHz, CDCl$_3$) δ: 1.02 (3H, t, J=7 Hz), 1.78–1.97 (2H, m), 3.82 (1H, br-s), 5.22 (2H, br-s), 5.29 (1H, d, J=16 Hz), 5.72 (1H, d, J=16 Hz), 7.55–7.75 (4H, m), 7.82–7.93 (4H, m), 8.15–8.24 (1H, m), 8.45 (1H, d, J=1 Hz).

IR (KBr): 3420, 1751, 1659, 1597, 1539 cm$^{-1}$.

EI-MS m/z: 508 (M$^+$).

Example 8

Preparation of Camptothecin (CPT) (Hydrogenolysis of 9-OTzC)

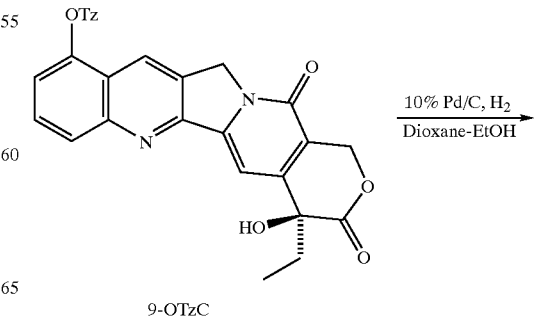

-continued

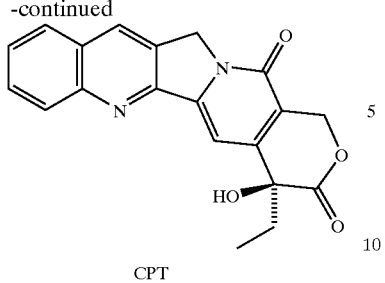

CPT

A solution of 9-(1-phenyl-5-tetrazolyloxy)camptothecin (9-OTzC; 100 mg, 0.39 mmol) in dioxane-ethanol (1:1) (20 ml) was added with 10% palladium/carbon (15 mg) and vigorously stirred at around 40° C. for 24 hr under hydrogen gas atmosphere. The catalyst was filtered off, and the filtrate was evaporated to dryness under reduced pressure. The residue was purified through silica gel column chromatography (chloroform containing 2% methanol to give camptothecin (CPT) (20 mg, yield 29%).

What is claimed is:

1. A process for preparing camptothecin, characterized in that it comprises the following steps (a) and (b);

(a) hydrolyzing 9-methoxycamptothecin or a natural material containing 9-methoxycamptothecin; and (a) hydrolyzing 9-methoxycamptothecin or a natural material containing 9-methoxycamptothecin; and (b) converting 9-hydroxycamptothecin obtained in the step (a) into camptothecin by 9-O-perfluoro-lower-alkylsulfonylation or 9-O-phenyltetrazolylation, followed by hydrogenolysis.

2. The process according to claim 1, characterized in that, in step (b), 9-hydroxycamptothecin is subjected to 9O-trifluoromethanesulfonylation.

3. The process according to claim 1, characterized in that said 9-hydroxycamptothecin is the 20(S) isomer and said camptothecin is 20(S)-camptothecin.

4. The process according to claim 2, characterized in that said 9-hydroxycamptothecin is the 20(S) isomer and said camptothecin is 20(S)-camptothecin.

* * * * *

UNITED STATES PATENT AND TRADEMARK OFFICE
CERTIFICATE OF CORRECTION

PATENT NO. : 6,743,918 B2
DATED : June 1, 2004
INVENTOR(S) : Yaegashi et al.

It is certified that error appears in the above-identified patent and that said Letters Patent is hereby corrected as shown below:

Column 12,
Lines 7 and 8, delete the duplicated "a".

Signed and Sealed this

Sixteenth Day of November, 2004

JON W. DUDAS
*Director of the United States Patent and Trademark Office*